United States Patent
Tai et al.

(10) Patent No.: US 7,412,090 B2
(45) Date of Patent: Aug. 12, 2008

(54) METHOD OF MANAGING WAFER DEFECTS

(75) Inventors: Hung-En Tai, Taipei Hsien (TW); Chia-Yun Chen, Kao-Hsiung Hsien (TW); Sheng-Jen Wang, Hsin-Chu (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 658 days.

(21) Appl. No.: 10/711,310

(22) Filed: Sep. 9, 2004

(65) Prior Publication Data

US 2006/0050950 A1 Mar. 9, 2006

(51) Int. Cl.
*G06K 9/00* (2006.01)

(52) U.S. Cl. .................. 382/145; 382/149; 700/110; 702/35; 348/126

(58) Field of Classification Search ............ 382/141, 382/145, 149, 152, 147; 118/730, 715; 700/121, 700/110, 109; 702/30, 122, 35; 356/394, 356/237.1, 238.3, 237.5, 388; 438/5; 257/E21.525, 257/E21.53; 348/126, 86, 125, 92

See application file for complete search history.

(56) References Cited

U.S. PATENT DOCUMENTS 6,744,266 B2 * 6/2004 Dor et al. ............. 324/751
6,763,130 B1 7/2004 Somekh et al.

FOREIGN PATENT DOCUMENTS

TW 484197 4/2002

* cited by examiner

*Primary Examiner*—Sheela C Chawan
(74) *Attorney, Agent, or Firm*—Winston Hsu

(57) ABSTRACT

A method of managing wafer defects includes inspecting each chip in a wafer to generate a unit of wafer defect raw data, using a server to integrate the unit of wafer defect raw data to generate a unit of wafer defect distribution data for recording positions, types, and sizes of defects, using the server to generate a corresponding drawing file according to the unit wafer defect distribution data to show all kinds of defect distributions, and transmitting the drawing file to a terminal such that terminal users can view the defect distributions without receiving the unit of wafer defect raw data.

6 Claims, 2 Drawing Sheets

METHOD OF MANAGING WAFER DEFECTS

BACKGROUND OF INVENTION

1. Field of the Invention

The invention relates to a method of managing wafer defects, and more particularly, to a method of managing wafer defects using a server to generate corresponding drawing files according to wafer defect raw data in advance for decreasing terminal calculations.

2. Description of the Prior Art

In the semiconductor manufacturing process, the semiconductor foundry performs defect inspection such as bright field or dark field defect inspection with wafers after a manufacturing process to improve wafer yield of the process. This kind of inspection is mostly performed on each chip on a wafer. In the inspection process, the inspection equipment takes an assigned position on a wafer as a standard position, and the inspection result of the standard position as a standard value to measure inspection results of another positions on the chip relative to the standard value and record them as the defect raw data. For integrating defect raw data corresponding to each chip on the same wafer, a complicated data transferring and handling process is taken. For example, defect raw data use the standard position of each chip as a standard value to record the defect distribution on other positions by the coordinates corresponding to the coordinates of the standard position on each chip. It is necessary to transfer coordinates to make the defect coordinates relative to each standard position of each chip be unified into the standard value of the origin of the wafer in order to integrate the defect distribution of the whole wafer while using the whole wafer viewpoint to observe the defect distribution. In the same way, the defect mode data such as size and type of defect also should be transferred to make the defect mode data of each chip be unified into a given data as the standard value to integrally display each defect mode on a whole wafer.

Semiconductor engineers are able to improve semiconductor equipments and wafer manufacturing steps according to the position, type, and size of each defect on a wafer after the defect raw data has been transferred integrally as mentioned before. This is the method of managing wafer defects.

In the prior art, semiconductor engineers use respective terminals to store these defect raw data and use the hardware resources of the terminal to perform the integral data transferring mentioned before to acquire the defect distribution data for each wafer. However, since the resolution of the inspection equipment is better and wafer sizes are increasing, a great quantity of defect raw data is generated after defect inspection. People who specialize in this technology know that the hardware resources of the terminal usually is not abundant for storing plenty of defect raw data and integrating the data efficiently. Furthermore, many engineers on different terminals may need to be notified of the defect distribution on the same wafer. If every terminal needs to perform data integration by itself, it will waste the hardware resources of each terminal and cause bad managing efficiency. In addition, plenty of wafer defect distribution drawings are not able to be integrated for engineers to analyze and compare each wafer completely.

SUMMARY OF INVENTION

The main purpose of the present invention is to provide a method of managing wafer defects to solve the above problem.

The present invention discloses a method of managing wafer defects including performing a inspection step to inspect defect on each chip on each wafer and generate wafer defect raw data, performing a data pre-treatment step by a server to integrally transfer wafer defect raw data according to each chip on the same wafer to generate a defect distribution data and record the distribution position, type, and size of each defect on the wafer, performing a drawing pre-treatment step by the server to generate a corresponding drawing file according to the new defect distribution position, and type, and size of each defect after wafer defect distribution data being transferred integrally to display each distribution mode of defect on each chip on the wafer by a drawing screen according to a drawing file, and performing a network management step to transmit the drawing file to a terminal without receiving the wafer defect raw data at the terminal such that a terminal user is capable of viewing the defect distributions on each chip on the wafer by the drawing screen according to the drawing file.

In other words, the method of managing wafer defects of the present invention handles defect raw data of each chip on each wafer integrally in advance with a server which has abundant hardware resources, and generates a corresponding drawing file according to wafer defect distribution. The terminal managing engineer is able to use a wafer as a unit to view the defect distribution for each wafer integrally by storing and reading the wafer defect drawing file directly, which is pre-treated by the server, from the terminal without performing data treatment using the terminal. Therefore, the present invention is capable of simplifying and reducing time for handling the wafer defect raw data. The managing engineer is able to view the wafer defect distribution efficiently by different types and sizes of defects to improve the yield of semiconductor process. Moreover, the method of managing wafer defects of the present invention is capable of displaying a plurality of wafer distribution drawings simultaneously to allow managing engineers to compare and analyze defect distribution of each wafer according to specific wafer lot number or process step.

These and other objectives of the present invention will no doubt become obvious to those of ordinary skill in the art after reading the following detailed description of the preferred embodiment that is illustrated in the various figures and drawings.

DETAILED DESCRIPTION

Figures 1, 2:
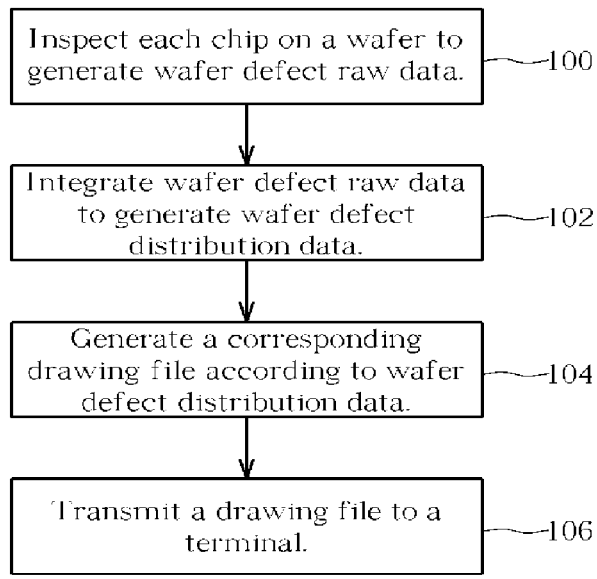
FIG. 1 is a flow chart of a method of managing wafer defects according to the present invention.
FIG. 2 is a schematic diagram of an analysis figure displaying drawing file of the drawing step in FIG. 1.

Please refer to FIG. 1. FIG. 1 is a flow chart of a method of managing wafer defects according to the present invention including:

Step 100: perform an inspection step to inspect defects on each chip on a wafer and generate corresponding wafer defect raw data;

Step 102: perform a data pre-treatment step with a server to integrate the wafer defect raw data of each chip on the same wafer and generate wafer defect distribution data for recording distribution position, type, and size of defects relative to the whole wafer;

Step 104: perform a drawing pre-treatment step with the server to generate a corresponding drawing file according to defect distribution data of each wafer to display each distribution mode of defects on each wafer; and Step 106: transmit the drawing file to a terminal with a server when the terminal engineer wants to view the wafer defect distribution such that these terminals do not need to receive the wafer defect raw data and terminal users are capable of viewing the defect distributions of each chip on the wafer according to the drawing file.

According to the above flow, at first the present invention performs an inspection step (step 100) to inspect defects on each chip of each wafer and generates corresponding wafer defect raw data which records each defect position relative to each die. The managing engineer performs a data pre-treatment step (step 102) with a server to integrally transfer the wafer defect raw data according to each chip on the same wafer and generate wafer defect distribution data such as transferring defect positions of defect raw data on each chip to the position relative to the origin of the wafer and records the wafer defect distribution data containing the position of defects on each chip relative to the origin of wafer, and the type and size of each chip. Furthermore, the inspection step is capable of performing defect inspection in at least two different inspection stations in sequence to generate corresponding wafer defect raw data. The data pre-treatment step further includes subtracting a defect position corresponding to a wafer defect raw data of an assigned inspection station from a defect position corresponding to a wafer defect raw data of the prior inspection station to generate a new defect data of the assigned inspection station and record the data in the wafer defect distribution data of the wafer.

The server according to the integrally transferred wafer distribution data performs a drawing pre-treatment step (step 104) to generate a corresponding drawing file according to a distribution position of new defects, the type, and the size of each defect and the drawing file is capable of displaying each defect distribution mode of each chip on the wafer with the drawing screen. At last, a network management step (step 106) is performed to transmit drawing files to terminals, and these terminals display the defect distribution mode of each chip on the wafer according to the drawing file with their respective drawing screens for terminal users to view. In this way, the terminals do not need to receive wafer defect raw data.

Figure 3:
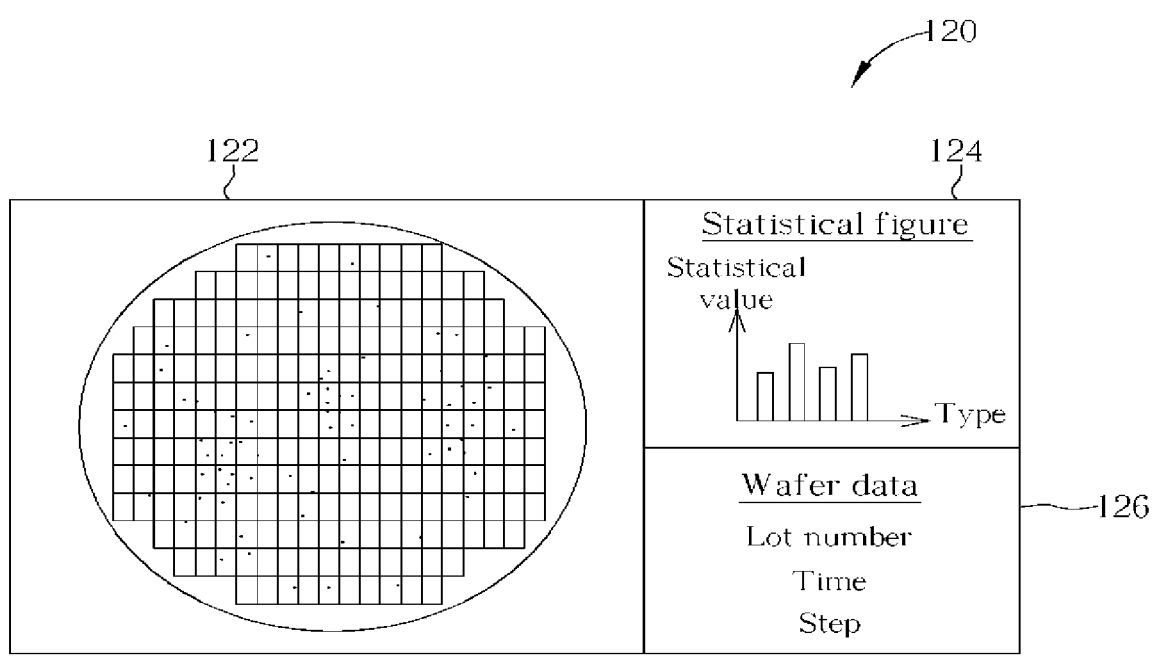
FIG. 3 is a schematic diagram of the displaying screen of the drawing file in FIG. 2.

Please refer to FIG. 2. FIG. 2 is a schematic diagram of a wafer data figure 110 presented by the drawing step in FIG. 1. In the present invention, the wafer data figure 110 displays a plurality of drawing files 114 according to a plurality of wafer data items 112. The wafer data items 112 include process time, wafer number, process step, and the wafer figure of each wafer. Each drawing file 114 uses a wafer figure icon 116 as a hyperlink to link with another displaying window to display the wafer figure of each wafer of the specific wafer data item 112 (drawing file of wafer defect distribution). Please refer to FIG. 3. FIG. 3 is a schematic diagram of the displaying screen 120 of the drawing file 114 in FIG. 2. Each drawing file 114 uses a hyperlink to link with the displaying screen 120 through the wafer figure icon 116. The displaying screen 120 uses a wafer figure 122 to present a wafer defect distribution, uses a statistical figure 124 to present wafer defect statistical data, and uses a wafer data 126 to present a wafer data item 112 corresponding to each drawing file 114. The file size of the drawing file 114 is smaller than the file size of total amount of all wafer defect raw data corresponding to a wafer. For example, the drawing file 114 is able to be transferred as a compressed drawing file, such as a JPEG, to a terminal, and the terminal is able to decompress the compressed drawing file to present the drawing file on the displaying screen 120 to terminal users. Moreover, the displaying screen 120 is capable of displaying a plurality of wafer figures 122 simultaneously for allowing managers to view the variation trend of each wafer defect distribution, and to allow managing engineers to compare and analyze each wafer defect distribution according to the specific wafer lot number and process step. For example, if defects gather in a specific corner on different wafers of the same lot number, it means that process step maybe has some problems on the corner. In the other words, the present invention presents defect distribution figures of different wafers to assist managing engineers with quickly discovering the process possible problems in a macroscopic view.

The present invention method of managing wafer defects involves the server generating corresponding drawing files in advance according to wafer defect data for presenting this information to managing engineers, and therefore simplifies and reduces the amount of time necessary for handling the wafer defect data. The managing engineer is able to view the wafer defect distribution efficiently by types and sizes of different defect to improve the yield of the semiconductor process. Moreover, the method of managing wafer defects of the present invention is capable of displaying a plurality of wafer distribution drawings simultaneously to allow managing engineers to compare and analyze defect distribution of each wafer according to the specific wafer lot number or process step.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for managing wafer defects comprising:
performing an inspection step to inspect defects on each chip of each wafer and generating corresponding wafer defect raw data;
performing a data pre-treatment step with a server to integrate the wafer defect raw data according to each chip of the same wafer and generate wafer defect distribution data for recording position, type, and size of defect;
performing a drawing pre-treatment step with the server to generate a corresponding drawing file according to a new position, type, and size of a defect after the wafer defect distribution data is transferred integrally to display each distribution mode of each defect on the wafer on a screen; and
performing a network management step to transmit the drawing file to a terminal without receiving the wafer defect raw data at the terminal such that a terminal user is capable of seeing the defect distributions of each chip of the wafer according to the drawing file on the drawing screen;
wherein the wafer defect raw data records a position of a wafer defect relative to a chip grid, the inspection step performs defect inspection in at least two different inspection stations in sequence to generate the corresponding wafer defect raw data, and the data pre-treatment step further comprises subtracting a defect position recorded by the wafer defect raw data of a prior wafer inspection station from the wafer defect raw data corresponding to a given wafer inspection station to generate the data of a new defect in the wafer inspection station and record the data of the new defect in the wafer defect distribution data.

2. The method of claim 1, wherein the wafer defect raw data records a position of a wafer defect relative to a chip grid, and the data pre-treatment step transfers the position of the wafer defect to a position corresponding to the origin of the wafer to make the wafer defect distribution data record the position of the wafer defect relative to the origin.

3. The method of claim 1, wherein the size of the drawing file generated by the server is smaller than the sum of all wafer defect raw data corresponding to a wafer.

4. The method of claim 1, wherein the drawing file generated by the server is compressed, and is uncompressed by the terminal.

5. The method of claim 1, wherein the data pre-treatment step is according to a plurality of wafers to generate corresponding wafer defect distribution data by the server and wherein the drawing pre-treatment step is according to a plurality of wafer defect distribution data to generate a corresponding drawing file by the server.

6. The method of claim 5, wherein the network management step includes transmitting a plurality of drawing files to the terminal, and the terminal displaying the plurality of drawing files simultaneously on the displaying screen to present a plurality of distribution modes of wafer defects.

* * * * *